United States Patent
O'Connor et al.

(10) Patent No.: US 12,396,939 B2
(45) Date of Patent: *Aug. 26, 2025

(54) SKIN CLEANSING FORMULATION

(71) Applicants: Dow Global Technologies LLC, Midland, MI (US); Rohm and Haas Company, Collegeville, PA (US)

(72) Inventors: Ying O'Connor, Coatesville, PA (US); Nikhil J. Fernandes, Philadelphia, PA (US); Emmett M. Partain, III, Bound Brook, NJ (US); Lyndsay M. Leal, Spring City, PA (US); Peilin Yang, Pearland, TX (US); Jennifer P. Todd, Willow Grove, PA (US)

(73) Assignees: Dow Global Technologies LLC, Midland, MI (US); ROHM AND HAAS COMPANY, Collegeville, PA (US)

( * ) Notice: Subject to any disclaimer, the term of this patent is extended or adjusted under 35 U.S.C. 154(b) by 374 days.

This patent is subject to a terminal disclaimer.

(21) Appl. No.: 17/794,365

(22) PCT Filed: Mar. 17, 2021

(86) PCT No.: PCT/US2021/022651
§ 371 (c)(1),
(2) Date: Jul. 21, 2022

(87) PCT Pub. No.: WO2021/194806
PCT Pub. Date: Sep. 30, 2021

(65) Prior Publication Data
US 2023/0096109 A1 Mar. 30, 2023

Related U.S. Application Data

(60) Provisional application No. 62/993,776, filed on Mar. 24, 2020.

(51) Int. Cl.
*A61K 8/00* (2006.01)
*A61K 8/41* (2006.01)
*A61K 8/73* (2006.01)
*A61K 8/92* (2006.01)
*A61Q 19/10* (2006.01)

(52) U.S. Cl.
CPC .......... *A61K 8/416* (2013.01); *A61K 8/73* (2013.01); *A61K 8/92* (2013.01); *A61Q 19/10* (2013.01); *A61K 2800/5426* (2013.01)

(58) Field of Classification Search
None
See application file for complete search history.

(56) References Cited

U.S. PATENT DOCUMENTS

| 4,411,891 | A | | 10/1983 | Mizutani et al. |
|---|---|---|---|---|
| 6,150,313 | A | * | 11/2000 | Harmalker ............... A61K 8/92 |
| | | | | 510/400 |
| 7,012,050 | B2 | * | 3/2006 | Harmalker ............ A61Q 19/10 |
| | | | | 510/121 |
| 8,518,387 | B2 | | 8/2013 | Drovetskaya et al. |
| 9,820,924 | B2 | * | 11/2017 | Pimenta ................ A61K 8/608 |
| 2010/0247472 | A1 | | 9/2010 | Sau |
| 2012/0021025 | A1 | | 1/2012 | Bendejacq et al. |
| 2015/0098920 | A1 | | 4/2015 | Stella et al. |
| 2015/0203598 | A1 | | 7/2015 | Andschutze et al. |
| 2018/0237816 | A1 | | 8/2018 | Paullin et al. |
| 2020/0323758 | A1 | | 10/2020 | Karagianni et al. |
| 2023/0093715 | A1 | | 3/2023 | Leal et al. |
| 2023/0108965 | A1 | | 4/2023 | Leal et al. |
| 2023/0117582 | A1 | | 4/2023 | Bai et al. |

FOREIGN PATENT DOCUMENTS

| CN | 106511133 | A | | 3/2017 |
|---|---|---|---|---|
| JP | H10279449 | A | | 10/1998 |
| JP | H11322555 | A | | 11/1999 |
| JP | 2000159642 | A | * | 6/2000 |
| JP | 3720964 | B2 | | 11/2005 |
| JP | 04712222 | B2 | | 6/2011 |
| WO | 2020009938 | | | 1/2010 |

OTHER PUBLICATIONS

UniversityofCambridge, 'Molecularweight,' webpage, pp. 1-4,May 3, 2011,retrievedfromInternetArchiveWaybackMachine.(Year: 2011) (Year: 2011).*
Database GNPD, Mintel, 2015, "Chinese Medicine Anti-Dandruff & Olive Moisturising Shampoo".
Database GNPD, Mintel, 2015, "Refresh Mint Cool Body Wash Gel".
Sibilia, "A Guide to Materials Characterization and Chemical Analysis", VCH, 1988, pp. 81-84.
Yau, Modern Size Exclusion Chromatography, Wiley-Interscience, 1979.

* cited by examiner

*Primary Examiner* — Necholus Ogden, Jr.
(74) *Attorney, Agent, or Firm* — Thomas S. Deibert

(57) ABSTRACT

A skin cleansing formulation is provided, comprising: a dermatologically acceptable vehicle; a dermatologically acceptable oil; and a deposition aid polymer, wherein the deposition aid polymer is a cationic dextran polymer, comprising a dextran polymer functionalized with quaternary ammonium groups; wherein the deposition aid polymer enhances the deposition of the dermatologically acceptable oil from the skin cleansing formulation onto mammalian skin.

13 Claims, No Drawings

SKIN CLEANSING FORMULATION

The present invention relates to a skin cleansing formulation. In particular, the present invention relates to a skin cleansing formulation containing a dermatologically acceptable vehicle; a dermatologically acceptable oil; and a deposition aid polymer, wherein the deposition aid polymer is a cationic dextran polymer, comprising a dextran polymer functionalized with quaternary ammonium groups; wherein the deposition aid polymer enhances the deposition of the dermatologically acceptable oil from the skin cleansing formulation onto mammalian skin.

Deposition of moisturizers is of particular interest for various personal care compositions. In particular, there is interest for personal care cleansers (e.g., body wash, face wash, hand wash, soap) that provide moisturizing benefits in addition to cleaning benefits.

Skin cleansing has become an ubiquitous component of personal hygiene. Cleansing of the skin facilitates the removal of dirt, germs and other things that are perceived as harmful to the skin or the individual. Cleansing formulations typically including a surfactant to promote the removal of materials deposited on the skin. Unfortunately, the cleansing formulations remove both undesirable and desirable materials from the skin. For example, cleansing formulations frequently undesirably remove oils from the skin, which oils operate to protect the skin from loss of moisture. Removal of too much oil from the skin may leave the skin vulnerable to becoming dry. One solution to this skin drying concern is the selection of mild surfactants. Another approach is to incorporate additives that help replace the oils removed through deposition; however, this approach has proven difficult in implementation, particularly in rinse off applications.

An approach to enhancing the deposition of materials on the skin is disclosed in United States Patent Application Publication No. 20100247472 to Sau. Sau disclose an aqueous personal care composition comprising a conditioner and a polymer functionalized with an amino group, wherein the amino group is pendant and the polymer functionalized with an amino group has the following structure:

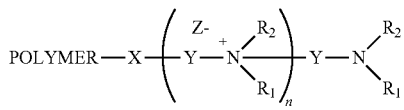

and, wherein the polymer comprises a natural, semisynthetic or synthetic polymer; X comprises an oxygen, nitrogen or sulfur atom, or a polyalkylene oxide group; Y comprises a bivalent polyalkylene or substituted bivalent polyalkylene moiety; $R_1$ and $R_2$ may be the same or different and comprise hydrogen, $C_{1-20}$ alkyl, $C_{1-20}$ aryl or $C_{1-20}$ alkyl(aryl) group; n comprises an integer between 0 and 10; $Z^-$ comprises a counter anion, and wherein the conditioner is selected from the group consisting of cationic surfactants, cationic polymers, nucleic acids, lipids, silicones, hydrocarbon oil, fatty esters and combinations thereof.

While conventionally used deposition aids such as soluble cationic modified celluloses (e.g., PQ-10), guar hydroxypropyl triammonium chloride and other cationic polymers (e.g., PQ-6, PQ-7) provide a certain level of oil deposition in personal care cleansers; they nevertheless exhibit low efficiency necessitating a relatively high oil incorporation into the personal care cleanser formulation to facilitate desired skin moisturization. Such high oil levels, however, detrimentally effect the foam/lathery in use consumer feel of the formulation.

Accordingly, there remains a need for personal care compositions that facilitate moisturization while maintaining desirable in use consumer feel.

The present invention provides a skin cleansing formulation, comprising: a dermatologically acceptable vehicle; a dermatologically acceptable oil; and a deposition aid polymer, wherein the deposition aid polymer is a cationic dextran polymer, comprising a dextran polymer functionalized with quaternary ammonium groups; wherein the deposition aid polymer enhances the deposition of the dermatologically acceptable oil from the skin cleansing formulation onto mammalian skin.

The present invention provides a method of making a skin cleansing formulation, comprising: (a) providing a dermatologically acceptable vehicle; (b) providing a dermatologically acceptable oil; (c) selecting a cationic dextran polymer to be a deposition aid for enhancing deposition of the dermatologically acceptable oil onto mammalian skin; wherein the cationic dextran polymer comprises a dextran polymer functionalized with quaternary ammonium groups; and (d) combining the dermatologically acceptable vehicle, the dermatologically acceptable oil and the cationic dextran polymer to form a skin cleansing formulation.

The present invention provides a method of depositing a dermatologically acceptable oil onto mammalian skin, comprising: providing a skin cleansing formulation according to the present invention; and applying the skin cleansing formulation to the skin of a mammal.

DETAILED DESCRIPTION

We have surprisingly found that cationic dextran polymer, comprising a dextran polymer functionalized with quaternary ammonium groups, wherein the deposition aid polymer enhances the deposition of the dermatologically acceptable oil from the skin cleansing formulation onto mammalian skin such that moisturization may be provided while maintaining desirable in use consumer feel.

Unless otherwise indicated, ratios, percentages, parts, and the like are by weight.

As used herein, unless otherwise indicated, the phrase "molecular weight" or Mw refers to the weight average molecular weight as measured in a conventional manner with gel permeation chromatography (GPC) and poly(ethylene oxide) standards. GPC techniques are discussed in detail in Modern Size Exclusion Chromatography, W. W. Yau, J. J. Kirkland, D. D. Bly; Wiley-Interscience, 1979, and in A Guide to Materials Characterization and Chemical Analysis, J. P. Sibilia; VCH, 1988, p. 81-84. Molecular weights are reported herein in units of Daltons, or equivalently, g/mol.

The term "dermatologically acceptable" as used herein and in the appended refers to ingredients that are typically used for topical application to the skin, and is intended to underscore that materials that are toxic when present in the amounts typically found in skin care compositions are not contemplated as part of the present invention.

Preferably, the skin cleansing formulation of the present invention is selected from the group consisting of a body wash formulation, an exfoliating body wash formulation, a facial wash formulation, an exfoliating facial wash formulation, a liquid hand soap, a soap, a sulfate-free cleansing formulation and a mild cleansing formulation. More preferably, the skin cleansing formulation of the present invention is selected from the group consisting of a body wash formulation, a facial wash formulation and a liquid hand soap. Most preferably, the skin cleansing formulation of the present invention is a body wash formulation.

Preferably, the skin cleansing formulation of the present invention, comprises: a dermatologically acceptable vehicle (preferably, wherein the skin cleansing formulation comprises 25 to 99 wt % (preferably, 30 to 95 wt %; more preferably, 40 to 90 wt %; most preferably, 70 to 85 wt %), based on weight of the skin cleansing formulation, of a dermatologically acceptable vehicle) (preferably, wherein the dermatologically acceptable vehicle comprises water; more preferably; wherein the dermatologically acceptable vehicle is selected from the group consisting of water and an aqueous $C_{1-4}$ alcohol mixture; most preferably, wherein the dermatologically acceptable vehicle is water); a dermatologically acceptable oil (preferably, wherein the skin cleansing formulation comprises 1 to 25 wt % (preferably, 2 to 20 wt %; more preferably, 2.5 to 15 wt %; most preferably, 4 to 6 wt %), based on weight of the skin cleansing formulation, of a dermatologically acceptable oil) (preferably, wherein the dermatologically acceptable oil is selected from the group consisting of hydrocarbon oils (e.g., mineral oil, petroleum jelly, polyisobutene, hydrogenated polyisobutene, hydrogenated polydecene, polyisohexadecane; natural oils (e.g., caprylic and capric triglyceride, sunflower oil, soybean oil, coconut oil); fragrance oils (e.g., limonene) and mixtures thereof; more preferably, wherein the dermatologically acceptable oil includes natural oil; most preferably, wherein the dermatologically acceptable oil is sunflower oil); and a deposition aid polymer (preferably, wherein the skin cleansing formulation comprises 0.05 to 5 wt % (preferably, 0.1 to 2.5 wt %; more preferably, 0.2 to 1 wt %; most preferably, 0.35 to 0.75 wt %), based on weight of the skin cleansing formulation, of the cationic dextran polymer), wherein the deposition aid polymer is a cationic dextran polymer, comprising a dextran polymer functionalized with quaternary ammonium groups; wherein the deposition aid polymer enhances the deposition of the dermatologically acceptable oil from the skin cleansing formulation onto mammalian skin.

Preferably, the skin cleansing formulation of the present invention is a liquid formulation. More preferably, the skin cleansing formulation of the present invention is an aqueous liquid formulation.

Preferably, the skin cleansing formulation of the present invention contains less than 0.001 wt %, based on weight of the skin cleansing formulation, of silicone. More preferably, the skin cleansing formulation of the present invention contains less than 0.0001 wt %, based on weight of the skin cleansing formulation, of silicone. Most preferably, the skin cleansing formulation of the present invention contains less than the detectable limit of silicone. Silicone includes, for example, dimethylpolysiloxane, methylphenyl polysiloxane, polyether denaturation silicone oil and poly amino modifying silicone oil.

Preferably, the skin cleansing formulation of the present invention, comprises a dermatologically acceptable vehicle. More preferably, the skin cleansing formulation of the present invention, comprises: 25 to 99 wt % (preferably, 30 to 95 wt %; more preferably, 40 to 90 wt %; most preferably, 70 to 85 wt %), based on weight of the skin cleansing formulation, of a dermatologically acceptable vehicle. Still more preferably, the skin cleansing formulation of the present invention, comprises: 25 to 99 wt % (preferably, 30 to 95 wt %; more preferably, 40 to 90 wt %; most preferably, 70 to 85 wt %), based on weight of the skin cleansing formulation, of a dermatologically acceptable vehicle; wherein the dermatologically acceptable vehicle comprises water. Yet more preferably, the skin cleansing formulation of the present invention, comprises: 25 to 99 wt % (preferably, 30 to 95 wt %; more preferably, 40 to 90 wt %; most preferably, 70 to 85 wt %), based on weight of the skin cleansing formulation, of a dermatologically acceptable vehicle, wherein the dermatologically acceptable vehicle is selected from the group consisting of water and an aqueous $C_{1-4}$ alcohol mixture. Most preferably, the skin cleansing formulation of the present invention, comprises: 25 to 99 wt % (preferably, 30 to 95 wt %; more preferably, 40 to 90 wt %; most preferably, 70 to 85 wt %), based on weight of the skin cleansing formulation, of a dermatologically acceptable vehicle, wherein the dermatologically acceptable vehicle is water.

Preferably, the water used in the skin cleansing formulation of the present invention is at least one of distilled water and deionized water. More preferably, the water used in the skin cleansing formulation of the present invention is distilled and deionized.

Preferably, the skin cleansing formulation of the present invention, comprises: a dermatologically acceptable oil. More preferably, the skin cleansing formulation of the present invention, comprises: 1 to 25 wt % (preferably, 2 to 20 wt %; more preferably, 2.5 to 15 wt %; most preferably, 4 to 6 wt %), based on weight of the skin cleansing formulation, of a dermatologically acceptable oil. Yet more preferably, the skin cleansing formulation of the present invention, comprises: 1 to 25 wt % (preferably, 2 to 20 wt %; more preferably, 2.5 to 15 wt %; most preferably, 4 to 6 wt %), based on weight of the skin cleansing formulation, of a dermatologically acceptable oil; wherein the dermatologically acceptable oil is selected from the group consisting of hydrocarbon oils (e.g., mineral oil, petroleum jelly, polyisobutene, hydrogenated polyisobutene, hydrogenated polydecene, polyisohexadecane; natural oils (e.g., caprylic and capric triglyceride, sunflower oil, soybean oil, coconut oil, argan oil, olive oil, almond oil); fragrance oils (e.g., limonene) and mixtures thereof. Still more preferably, the skin cleansing formulation of the present invention, comprises: 1 to 25 wt % (preferably, 2 to 20 wt %; more preferably, 2.5 to 15 wt %; most preferably, 4 to 6 wt %), based on weight of the skin cleansing formulation, of a dermatologically acceptable oil; wherein the dermatologically acceptable oil includes at least one of petroleum jelly, mineral oil and sunflower oil. Most preferably, the skin cleansing formulation of the present invention, comprises: 1 to 25 wt % (preferably, 2 to 20 wt %; more preferably, 2.5 to 15 wt %; most preferably, 4 to 6 wt %), based on weight of the skin cleansing formulation, of a dermatologically acceptable oil; wherein the dermatologically acceptable oil is sunflower oil.

Preferably, the skin cleansing formulation of the present invention comprises a deposition aid polymer, wherein the deposition aid polymer is a cationic dextran polymer, comprising a dextran polymer functionalized with quaternary ammonium groups; wherein the deposition aid polymer enhances deposition of the dermatologically acceptable oil from the skin cleansing formulation onto mammalian skin. More preferably, the skin cleansing formulation of the present invention comprises 0.05 to 5 wt % (preferably, 0.1 to 2.5 wt %; more preferably, 0.2 to 1 wt %; most preferably, 0.35 to 0.75 wt %), based on weight of the skin cleansing formulation, of a deposition aid polymer; wherein the deposition aid polymer is a cationic dextran polymer, comprising a dextran polymer functionalized with quaternary ammonium groups; wherein the deposition aid polymer enhances deposition of the dermatologically acceptable oil from the skin cleansing formulation onto mammalian skin. Most preferably, the skin cleansing formulation of the present invention comprises 0.05 to 5 wt % (preferably, 0.1 to 2.5 wt %; more preferably, 0.2 to 1 wt %; most preferably, 0.35 to 0.75 wt %), based on weight of the skin cleansing formulation, of a deposition aid polymer; wherein the deposition aid polymer is a cationic dextran polymer, comprising a dextran polymer functionalized with quaternary ammonium groups; wherein the deposition aid polymer has a Kjeldahl nitrogen content corrected for ash and volatiles, TKN, of 0.5 to 4.0 wt % (preferably, 0.75 to 3.25 wt %; more preferably, 0.9 to 2.6 wt %; most preferably, 1 to 2.0 wt %) (measured using a Buchi KjelMaster K-375 automated analyzer, corrected for volatiles and ash measured as described in ASTM method D-2364); and wherein the deposition aid polymer enhances deposition of the dermatologically acceptable oil from the skin cleansing formulation onto mammalian skin.

Preferably, the deposition aid polymer is a dextran polymer functionalized with quaternary ammonium moieties. More preferably, the deposition aid polymer is a dextran polymer functionalized with quaternary ammonium moieties; wherein the dextran polymer is a branched chain dextran polymer. Still more preferably, the deposition aid polymer is a dextran polymer functionalized with quaternary ammonium moieties; wherein the dextran polymer comprises a branched chain dextran polymer; wherein the branched chain dextran polymer comprises a plurality of glucose structural units; wherein 90 to 98 mol % (preferably, 92.5 to 97.5 mol %; more preferably, 93 to 97 mol %; most preferably, 94 to 96 mol %) of the glucose structural units are connected by $\alpha$-D-1,6 linkages and 2 to 10 mol % (preferably, 2.5 to 7.5 mol %; more preferably, 3 to 7 mol %; most preferably, 4 to 6 mol %) of the glucose structural units are connected by $\alpha$-1,3 linkages. Most preferably, the deposition aid polymer is a dextran polymer functionalized with quaternary ammonium moieties; wherein the dextran polymer is a branched chain dextran polymer; wherein the branched chain dextran polymer comprises a plurality of glucose structural units; wherein 90 to 98 mol % (preferably, 92.5 to 97.5 mol %; more preferably, 93 to 97 mol %; most preferably, 94 to 96 mol %) of the glucose structural units are connected by $\alpha$-D-1,6 linkages and 2 to 10 mol % (preferably, 2.5 to 7.5 mol %; more preferably, 3 to 7 mol %; most preferably, 4 to 6 mol %) of the glucose structural units are connected by $\alpha$-1,3 linkages according to formula (i)

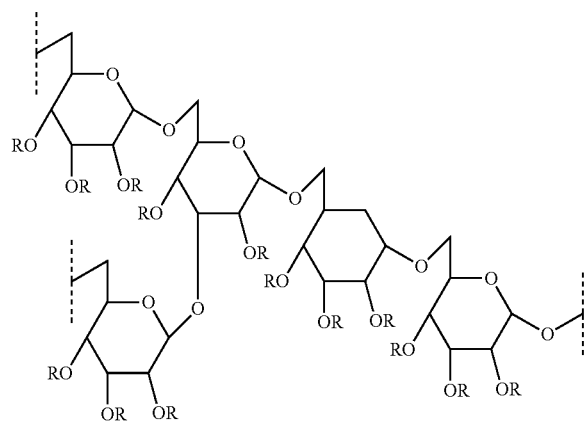

(i)

wherein R is selected from a hydrogen, a $C_{1-4}$ alkyl group and a hydroxy $C_{1-4}$ alkyl group; and wherein the average branch off the dextran polymer backbone is ≤3 anhydroglucose units.

Preferably, the dextran polymer contain less than 0.01 wt %, based on weight of the dextran polymer, of alternan. More preferably, the dextran polymer contain less than 0.001 wt %, based on weight of the dextran polymer, of alternan. Most preferably, the dextran polymer contain less than the detectable limit of alternan.

Preferably, the deposition aid polymer is a dextran polymer functionalized with quaternary ammonium moieties; wherein the quaternary ammonium moieties are selected from the group consisting of at least one of (a) a dextran crosslinking group of formula (A)

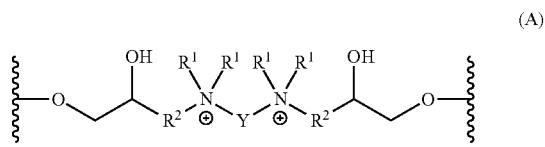

(A)

and (b) a quaternary ammonium group of formula (B)

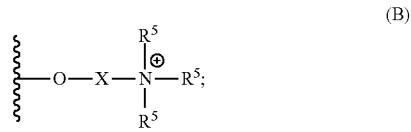

(B)

wherein

is a pendant oxygen on the dextran polymer; wherein each $R^1$ is independently selected from a substituted or unsubstituted $C_{1-6}$ alkyl group (wherein "substituted" means that the group in question contains at least one of a halogen, a hydroxy group, an amino group or a carboxy group) (preferably, wherein each $R^1$ is independently selected from an unsubstituted $C_{1-6}$ alkyl group; more preferably, wherein each $R^1$ is independently selected from the group consisting of a methyl group, an ethyl group, a propyl group, an isopropyl group, a butyl group, an isobutyl group, a tert-butyl group, a sec-butyl group, a pentyl group, an isopentyl group, a neopentyl group, a hexyl group and an isohexyl group; still more preferably, wherein each $R^1$ is independently selected from the group consisting of a methyl group, an ethyl group, a propyl group, an isopropyl group, a butyl group, an isobutyl group, a tert-butyl group and a sec-butyl group; yet more preferably, wherein each $R^1$ is independently selected from the group consisting of a methyl group, an ethyl group, a propyl group and an isopropyl group; yet still more preferably, wherein each $R^1$ is independently selected from the group consisting of a methyl group and an ethyl group; most preferably, wherein each $R^1$ is a methyl group); wherein each $R^2$ is independently selected from the group consisting of a $C_{1-6}$ alkanediyl group (preferably, wherein each $R^2$ is independently selected from the group consisting of a $C_{1-4}$ alkanediyl group; more preferably, wherein each $R^2$ is independently selected from the group consisting of a $C_{1-2}$ alkanediyl group; most preferably, wherein each $R^2$ is a —$CH_2$— group); wherein Y is a divalent bridging group (preferably, wherein Y is a divalent bridging group selected from the group consisting of a $C_{1-6}$ alkanediyl group and a —$R^3$—O—$R^4$— group; more preferably, wherein Y is a —$R^3$—O—$R^4$— group); wherein $R^3$ and $R^4$ are independently selected from the group consisting of a $C_{1-6}$ alkanediyl group (preferably, wherein $R^3$ and $R^4$ are independently selected from the group consisting of a $C_{1-4}$ alkanediyl group; more preferably, wherein $R^3$ and $R^4$ are independently selected from the group consisting of a $C_{1-3}$ alkanediyl group; most preferably, wherein $R^3$ and $R^4$ are both a —$CH_2CH_2$— group)(preferably, wherein $R^3$ and $R^4$ are the same); wherein X is a divalent linking group bonding the quaternary ammonium moiety to the pendent oxygen on the dextran polymer (preferably, wherein X is selected from divalent hydrocarbon groups, which may optionally be substituted (e.g., with a hydroxy group, an alkoxy group, an ether group); more preferably, wherein X is a —$CH_2CH(OR^6)CH_2$— group, wherein $R^6$ is selected from the group consisting of a hydrogen and a $C_{1-4}$ alkyl group; most preferably, wherein X is a —$CH_2CH(OH)CH_2$— group); and wherein each $R^5$ is independently selected from the group consisting of a $C_{1-22}$ alkyl group (preferably, wherein each $R^5$ is independently selected from the group consisting of a $C_{1-3}$ alkyl group and a $C_{6-22}$ alkyl group; more preferably, wherein each $R^5$ is independently selected from the group consisting of a methyl group and an ethyl group; most preferably, wherein each $R^5$ is a methyl group).

More preferably, the deposition aid polymer is a dextran polymer functionalized with quaternary ammonium moieties; wherein the quaternary ammonium moieties are selected from the group consisting of at least one of (a) a dextran crosslinking group of formula (A) and (b) a quaternary ammonium group of formula (B); wherein the dextran crosslinking group of formula (A) is of Formula (C)

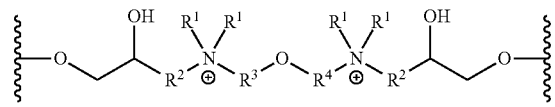

(C)

and wherein the quaternary ammonium group of formula (B) is of formula (D)

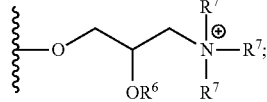

(D)

wherein

is a pendant oxygen on the dextran polymer; wherein each $R^1$ is independently selected from a substituted or unsubstituted $C_{1-6}$ alkyl group (wherein "substituted" means that the group in question contains at least one moiety selected from a halogen, a hydroxy group, an amino group or a carboxy group) (preferably, wherein each $R^1$ is independently selected from an unsubstituted $C_{1-6}$ alkyl group; more preferably, wherein each $R^1$ is independently selected from the group consisting of a methyl group, an ethyl group, a propyl group, an isopropyl group, a butyl group, an isobutyl group, a tert-butyl group, a sec-butyl group, a pentyl group, an isopentyl group, a neopentyl group, a hexyl group and an isohexyl group; still more preferably, wherein each $R^1$ is independently selected from the group consisting of a methyl group, an ethyl group, a propyl group, an isopropyl group, a butyl group, an isobutyl group, a tert-butyl group and a sec-butyl group; yet more preferably, wherein each $R^1$ is independently selected from the group consisting of a methyl group, an ethyl group, a propyl group and an isopropyl group; yet still more preferably, wherein each $R^1$ is independently selected from the group consisting of a methyl group and an ethyl group; most preferably, wherein each $R^1$ is a methyl group); wherein each $R^2$ is independently selected from the group consisting of a $C_{1-6}$ alkanediyl group (preferably, wherein each $R^2$ is a $C_{1-4}$ alkanediyl group; more preferably, wherein each $R^2$ is a $C_{1-2}$ alkanediyl group; most preferably, wherein each $R^2$ is a —$CH_2$— group); wherein $R^3$ and $R^4$ are independently selected from the group consisting of a $C_{1-6}$ alkanediyl group (preferably, wherein $R^3$ and $R^4$ are independently selected from the group consisting of a $C_{1-4}$ alkanediyl group; more preferably, wherein $R^3$ and $R^4$ are independently selected from the group consisting of a $C_{1-3}$ alkanediyl group; most preferably, a —$CH_2CH_2$— group)(preferably, wherein $R^3$ and $R^4$ are the same); wherein each $R^6$ is selected from the group consisting of a hydrogen and a $C_{1-4}$ alkyl group (preferably, wherein $R^6$ is a hydrogen); and wherein each $R^7$ is independently selected from the group consisting of a methyl group and an ethyl group (preferably, a methyl group).

Still more preferably, the deposition aid polymer is a dextran polymer functionalized with quaternary ammonium moieties; wherein the quaternary ammonium moieties are selected from the group consisting of at least one of (a) a dextran crosslinking group of formula (A) and (b) a quaternary ammonium group of formula (B); wherein the dextran crosslinking group of formula (A) is selected from the group consisting of

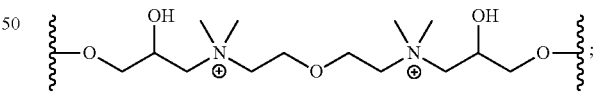

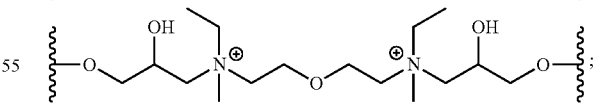

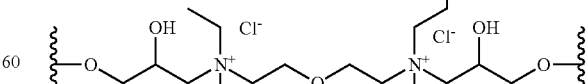

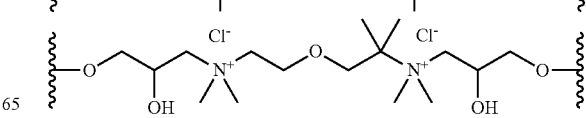

and mixtures thereof; and wherein the quaternary ammonium group of formula (B) is of formula (D); wherein

is a pendant oxygen on the dextran polymer; wherein each $R^6$ is selected from the group consisting of a hydrogen and a $C_{1-4}$ alkyl group (preferably, wherein $R^6$ is a hydrogen); and wherein each $R^7$ is independently selected from the group consisting of a methyl group and an ethyl group (preferably, a methyl group).

Most preferably, the deposition aid polymer is a dextran polymer functionalized with quaternary ammonium moieties; wherein the quaternary ammonium moieties are selected from the group consisting of (b) a quaternary ammonium group of formula (D); wherein

is a pendant oxygen on the dextran polymer; wherein each $R^6$ is selected from the group consisting of a hydrogen and a $C_{1-4}$ alkyl group (preferably, wherein $R^6$ is a hydrogen); and wherein each $R^7$ is independently selected from the group consisting of a methyl group and an ethyl group (preferably, a methyl group).

Preferably, the deposition aid polymer comprises <0.001 meq/gram (preferably, <0.0001 meq/gram; more preferably, <0.00001 meq/gram; most preferably, <detectable limit) of aldehyde functionality.

Preferably, the deposition aid polymer comprises <0.1% (preferably, <0.01%; more preferably, <0.001%; most preferably, <detectable limit), of the linkages between individual glucose units in the deposition aid polymer are β-1,4 linkages.

Preferably, the deposition aid polymer comprises <0.1% (preferably, <0.01%; more preferably, <0.001%; most preferably, <detectable limit), of the linkages between individual glucose units in the deposition aid polymer are β-1,3 linkages.

Preferably, the deposition aid polymer comprises <0.001 meq/gram (preferably, <0.0001 meq/gram; more preferably, <0.00001 meq/gram; most preferably, <detectable limit) of silicone containing functionality.

Preferably, the deposition aid polymer comprises <0.1 mol % (preferably, 0 to <0.01 mol %; more preferably, 0 to <0.001 mol %; most preferably, 0 to <detectable limit) of structural units of a reactive siloxane, wherein the structural units of a reactive siloxane include Si—O moieties. More preferably, the deposition aid polymer comprises <0.1 mol % (preferably, 0 to <0.01 mol %; more preferably, 0 to <0.001 mol %; most preferably, 0 to <detectable limit) of structural units of a reactive siloxane, wherein the structural units of a reactive siloxane include Si—O moieties; wherein the reactive siloxane is a polymer which may comprise one or more functional moieties selected from the group consisting of amino, amido, alkoxy, hydroxy, polyether, carboxy, hydride, mercapto, sulfate phosphate, and/or quaternary ammonium moieties—these moieties may be attached directly to the siloxane backbone through a bivalent alkylene radical, (i.e., pendant) or may be part of the backbone.

Preferably, the skin cleansing formulation of the present invention further comprises a dermatologically acceptable personal care cleansing surfactant. More preferably, the skin cleansing formulation of the present invention further comprises 0.01 to 80 wt % (preferably, 5 to 50 wt %; more preferably, 7.5 to 35 wt %, most preferably, 10 to 20 wt %), based on weight of the skin cleansing formulation, of a dermatologically acceptable personal care cleansing surfactant. Still more preferably, the skin cleansing formulation of the present invention further comprises 0.01 to 80 wt % (preferably, 5 to 50 wt %; more preferably, 7.5 to 35 wt %, most preferably, 10 to 20 wt %), based on weight of the skin cleansing formulation, of a dermatologically acceptable personal care cleansing surfactant; wherein the dermatologically acceptable personal care cleansing surfactant is selected from the group consisting of alkyl polyglucosides (e.g., lauryl glucoside, coco-glucoside, decyl glucoside), glycinates (e.g., sodium cocoyl glycinate), betaines (e.g., alkyl betaines such as cetyl betaine and amido betaines such as cocamidopropyl betaine), taurates (e.g., sodium methyl cocoyl taurate), glutamates (e.g., sodium cocoyl glutamate), sarcosinates (e.g., sodium lauroyl sarcosinate), isethionates (e.g., sodium cocoyl isethionate, sodium lauroyl methyl isethionate), sulfoacetates (e.g., sodium lauryl sulfoacetate), alaninates (e.g., sodium cocoyl alaninate), amphoacetates (e.g., sodium cocoamphoacetate), sulfates (e.g., sodium laureth sulfate), sulfonates (e.g., sodium $C_{14-16}$ olefin sulfonate), succinates (e.g., disodium lauryl sulfosuccinate) and mixtures thereof. Most preferably, the skin cleansing formulation of the present invention further comprises 0.01 to 80 wt % (preferably, 5 to 50 wt %; more preferably, 7.5 to 35 wt %, most preferably, 10 to 20 wt %), based on weight of the skin cleansing formulation, of a dermatologically acceptable personal care cleansing surfactant; wherein the dermatologically acceptable personal care cleansing surfactant comprises a mixture of sodium laureth sulfate (SLES) and cocamidopropyl betaine.

Preferably, the skin cleansing formulation of the present invention, optionally, further comprises at least one additional ingredient selected from the group consisting of an antimicrobial agent; a rheology modifier; a soap; a colorant; pH adjusting agent; an antioxidant (e.g., butylated hydroxytoluene); a humectant (e.g., glycerin, sorbitol, monoglycerides, lecithins, glycolipids, fatty alcohols, fatty acids, polysaccharides, sorbitan esters, polysorbates (e.g., Polysorbate 20, Polysorbate 40, Polysorbate 60, and Polysorbate 80), diols (e.g., propylene glycol), diol analogs, triols, triol analogs, cationic polymeric polyols); a wax; a foaming agent; an emulsifying agent; a fragrance; a chelating agent; a preservative (e.g., benzoic acid, sorbic acid, phenoxyethanol); a bleaching agent; a lubricating agent; a sensory modifier; a sunscreen additive; a vitamin; a protein/amino acid; a plant extract; a natural ingredient; a bioactive agent; an anti-aging agent; a penetrant; an anti-static agent; an absorbent; a hard particle; a soft particle; a slip agent; an opacifier; a pearlizing agent; a salt and mixtures thereof. More preferably, the skin cleansing formulation of the present invention, optionally, further comprises at least one additional ingredient selected from the group consisting of at least one of an antimicrobial agent, a dermatologically acceptable personal care cleansing surfactant, a rheology modifier, a soap, a colorant and a pH adjusting agent.

Preferably, the skin cleansing formulation of the present invention further comprises an antimicrobial agent. More preferably, the skin cleansing formulation of the present invention further comprises an antimicrobial agent, wherein the antimicrobial agent is selected from the group consisting of phenoxyethanol, benzoic acid, benzyl alcohol, sodium benzoate, DMDM hydantoin, 2-ethylhexyl glyceryl ether and isothiazolinone (e.g., methylchloroisothiazolinone, methylisothiazolinone). Still more preferably, the skin cleansing formulation of the present invention, further comprises an antimicrobial agent, wherein the antimicrobial agent is an isothiazolinone (more preferably, wherein the antimicrobial is selected from the group consisting of methylisothiazolinone, methylchloroisothiazolinone and mixtures thereof; most preferably, wherein the biocide is methylisothiazolinone). Most preferably, the skin cleansing formulation of the present invention, further comprises an antimicrobial agent, wherein the antimicrobial agent is an isothiazolinone (more preferably, wherein the antimicrobial agent is selected from the group consisting of methylisothiazolinone, methylchloroisothiazolinone and mixtures thereof; most preferably, wherein the antimicrobial agent is methylisothiazolinone); and wherein the skin cleansing formulation is a body wash formulation.

Preferably, the skin cleansing formulation of the present invention further comprises a soap. More preferably, the skin cleansing formulation of the present invention further comprises a soap, wherein the soap is selected from the group consisting of sodium stearate, sodium laurate, sodium tallowate, sodium palmitate, potassium stearate, potassium laurate, potassium tallowate, potassium palmitate and mixtures thereof. Still more preferably, the skin cleansing formulation of the present invention further comprises a soap, wherein the soap is selected from the group consisting of sodium stearate, sodium laurate, potassium stearate, potassium laurate and mixtures thereof. Yet more preferably, the skin cleansing formulation of the present invention further comprises a soap, wherein the soap is selected from the group consisting of sodium stearate, potassium stearate and mixtures thereof. Most preferably, the skin cleansing formulation of the present invention further comprises a soap, wherein the soap comprises sodium stearate.

Preferably, the skin cleansing formulation of the present invention, further comprises a soap, wherein the soap is selected from the group consisting of sodium stearate, sodium laurate, sodium tallowate, sodium palmitate, potassium stearate, potassium laurate, potassium tallowate, potassium palmitate and mixtures thereof (more preferably, wherein the soap is selected from the group consisting of sodium stearate, sodium laurate, potassium stearate, potassium laurate and mixtures thereof; still more preferably, wherein the soap is selected from the group consisting of sodium stearate, potassium stearate and mixtures thereof; most preferably, wherein the soap is sodium stearate); and wherein the skin cleansing formulation is a body wash formulation.

Preferably, the skin cleansing formulation of the present invention further comprises a rheology modifier. More preferably, the skin cleansing formulation of the present invention further comprises a rheology modifier; wherein the rheology modifier is selected from the group consisting of sodium chloride, cellulose, xanthan gum, an acrylates copolymer and mixtures thereof. Still more preferably, the skin cleansing formulation of the present invention further comprises a rheology modifier; wherein the rheology modifier includes an acrylates copolymer; wherein the acrylates copolymer is an ionic acrylic based rheology modifier. Yet more preferably, the skin cleansing formulation of the present invention further comprises a rheology modifier; wherein the rheology modifier is an acrylates copolymer is an alkali-swellable anionic acrylic copolymer (e.g., Aculyn™ 33, Aculyn™ 22, Aculyn™ 28, Aculyn™ 88 rheology modifiers all available from The Dow Chemical Company). Most preferably, the skin cleansing formulation of the present invention further comprises a rheology modifier; wherein the skin cleansing formulation is a body wash formulation and wherein the rheology modifier is an alkali-swellable anionic acrylic copolymer (e.g., Aculyn™ 33, Aculyn™ 22, Aculyn™ 28, Aculyn™ 88 rheology modifiers all available from The Dow Chemical Company).

Preferably, the skin cleansing formulation of the present invention further comprises a pH adjusting agent. More preferably, the skin cleansing formulation of the present invention, further comprises a pH adjusting agent, wherein the skin cleansing formulation is a body wash formulation. Most preferably, the skin cleansing formulation of the present invention, further comprises a pH adjusting agent, wherein the skin cleansing formulation is a body wash formulation and wherein the body wash formulation has a pH of 4.5 to 9 (preferably, 5 to 8; most preferably, 6 to 7).

Preferably, the pH adjusting agent is selected from the group consisting of at least one of citric acid, lactic acid, hydrochloric acid, aminoethyl propanediol, triethanolamine, monoethanolamine, sodium hydroxide, potassium hydroxide, amino-2-methyl-1-propanol. More preferably, the pH adjusting agent is selected from the group consisting of at least one of citric acid, lactic acid, sodium hydroxide, potassium hydroxide, triethanolamine, amino-2-methyl-1-propanol. Still more preferably, the pH adjusting agent includes is triethanolamine Most preferably, the pH adjusting agent is triethanolamine.

Preferably, the skin cleansing formulation of the present invention further comprises a colorant. More preferably, the skin cleansing formulation of the present invention, further comprises a colorant, wherein the skin cleansing formulation is a body wash formulation.

Preferably, the skin cleansing formulation of the present invention is a body wash formulation. More preferably, the skin cleansing formulation of the present invention is a body wash formulation, comprising: 25 to 99 wt % (preferably, 30 to 90 wt %; more preferably, 60 to 85 wt %; most preferably, 75 to 80 wt %), based on weight of the skin cleansing formulation, of a dermatologically acceptable vehicle (preferably, water); 0.05 to 5 wt % (preferably, 0.1 to 2.5 wt %; more preferably, 0.2 to 1 wt %; most preferably, 0.35 to 0.75 wt %), based on weight of the skin cleansing formulation, of a deposition aid polymer, wherein the deposition aid polymer is a cationic dextran polymer, comprising a dextran functionalized with quaternary ammonium groups; 0.5 to 40 wt % (preferably, 1 to 15 wt %; more preferably, 2.5 to 7.5 wt %), based on weight of the skin cleansing formulation, of a dermatologically acceptable oil. Still more preferably, the skin cleansing formulation of the present invention is a body wash formulation, comprising 25 to 99 wt % (preferably, 30 to 90 wt %; more preferably, 60 to 85 wt %; most preferably, 75 to 80 wt %), based on weight of the skin cleansing formulation, of a dermatologically acceptable vehicle (preferably, water); 0.05 to 5 wt % (preferably, 0.1 to 2.5 wt %; more preferably, 0.2 to 1 wt %; most preferably, 0.35 to 0.75 wt %), based on weight of the skin cleansing formulation, of a deposition aid polymer, wherein the deposition aid polymer is a cationic dextran polymer, comprising a dextran functionalized with quaternary ammonium groups; 0.5 to 40 wt % (preferably, 1 to 15 wt %; more preferably, 2.5 to 7.5 wt %), based on weight of the skin cleansing formulation, of a dermatologically acceptable oil; wherein the dermatologically acceptable oil is selected from the group consisting of hydrocarbon oils (e.g., mineral oil, petroleum jelly); natural oils (e.g., sunflower oil, soybean oil, coconut oil); silicone oils (e.g., polydimethylsiloxane); fragrance oils (e.g., limonene) and mixtures thereof. Yet more preferably, the skin cleansing formulation of the present invention is a body wash formulation, comprising 25 to 99 wt % (preferably, 30 to 90 wt %; more preferably, 60 to 85 wt %; most preferably, 75 to 80 wt %), based on weight of the skin cleansing formulation, of a dermatologically acceptable vehicle (preferably, water); 0.05 to 5 wt % (preferably, 0.1 to 2.5 wt %; more preferably, 0.2 to 1 wt %; most preferably, 0.35 to 0.75 wt %), based on weight of the skin cleansing formulation, of a deposition aid polymer, wherein the deposition aid polymer is a cationic dextran polymer, comprising a dextran functionalized with quaternary ammonium groups; 0.5 to 40 wt % (preferably, 1 to 15 wt %; more preferably, 2.5 to 7.5 wt %), based on weight of the skin cleansing formulation, of a dermatologically acceptable oil; wherein the dermatologically acceptable oil is selected from the group consisting of at least one of mineral oil, petroleum jelly, sunflower oil, soybean oil, coconut oil, silicone oil and fragrance oil. Yet still more preferably, the skin cleansing formulation of the present invention is a body wash formulation, comprising 25 to 99 wt % (preferably, 30 to 90 wt %; more preferably, 60 to 85 wt %; most preferably, 75 to 80 wt %), based on weight of the skin cleansing formulation, of a dermatologically acceptable vehicle (preferably, water); 0.05 to 5 wt % (preferably, 0.1 to 2.5 wt %; more preferably, 0.2 to 1 wt %; most preferably, 0.35 to 0.75 wt %), based on weight of the skin cleansing formulation, of a deposition aid polymer, wherein the deposition aid polymer is a cationic dextran polymer, comprising a dextran functionalized with quaternary ammonium groups; 0.5 to 40 wt % (preferably, 1 to 15 wt %; more preferably, 2.5 to 7.5 wt %), based on weight of the skin cleansing formulation, of a dermatologically acceptable oil; wherein the dermatologically acceptable oil includes sunflower oil. Most preferably, the skin cleansing formulation of the present invention is a body wash formulation, comprising 25 to 99 wt % (preferably, 30 to 90 wt %; more preferably, 60 to 85 wt %; most preferably, 75 to 80 wt %), based on weight of the skin cleansing formulation, of a dermatologically acceptable vehicle (preferably, water); 0.05 to 5 wt % (preferably, 0.1 to 2.5 wt %; more preferably, 0.2 to 1 wt %; most preferably, 0.35 to 0.75 wt %), based on weight of the skin cleansing formulation, of a deposition aid polymer, wherein the deposition aid polymer is a cationic dextran polymer, comprising a dextran functionalized with quaternary ammonium groups; 0.5 to 40 wt % (preferably, 1 to 15 wt %; more preferably, 2.5 to 7.5 wt %), based on weight of the skin cleansing formulation, of a dermatologically acceptable oil; wherein the dermatologically acceptable oil is sunflower oil.

Preferably, the skin cleansing formulation of the present invention is a body wash formulation. More preferably, the skin cleansing formulation of the present invention is a body wash formulation, comprising: 25 to 99 wt % (preferably, 30 to 90 wt %; more preferably, 60 to 85 wt %; most preferably, 75 to 80 wt %), based on weight of the skin cleansing formulation, of a dermatologically acceptable vehicle (preferably, water); 0.05 to 5 wt % (preferably, 0.1 to 2.5 wt %; more preferably, 0.2 to 1 wt %; most preferably, 0.35 to 0.75 wt %), based on weight of the skin cleansing formulation, of a deposition aid polymer, wherein the deposition aid polymer is a cationic dextran polymer, comprising a dextran functionalized with quaternary ammonium groups; 0.5 to 40 wt % (preferably, 1 to 15 wt %; more preferably, 2.5 to 7.5 wt %), based on weight of the skin cleansing formulation, of a dermatologically acceptable oil; and 0.01 to 80 wt % (more preferably, 5 to 50 wt %; still more preferably, 7.5 to 35 wt %, most preferably, 10 to 20 wt %), based on weigh of the skin cleansing formulation, of a dermatologically acceptable personal care cleansing surfactant. Still more preferably, the skin cleansing formulation of the present invention is a body wash formulation, comprising 25 to 99 wt % (preferably, 30 to 90 wt %; more preferably, 60 to 85 wt %; most preferably, 75 to 80 wt %), based on weight of the skin cleansing formulation, of a dermatologically acceptable vehicle (preferably, water); 0.05 to 5 wt % (preferably, 0.1 to 2.5 wt %; more preferably, 0.2 to 1 wt %; most preferably, 0.35 to 0.75 wt %), based on weight of the skin cleansing formulation, of a deposition aid polymer, wherein the deposition aid polymer is a cationic dextran polymer, comprising a dextran functionalized with quaternary ammonium groups; 0.5 to 40 wt % (preferably, 1 to 15 wt %; more preferably, 2.5 to 7.5 wt %), based on weight of the skin cleansing formulation, of a dermatologically acceptable oil; wherein the dermatologically acceptable oil is selected from the group consisting of hydrocarbon oils (e.g., mineral oil, petroleum jelly); natural oils (e.g., sunflower oil, soybean oil, coconut oil); silicone oils (e.g., polydimethylsiloxane); fragrance oils (e.g., limonene) and mixtures thereof; and 0.01 to 80 wt % (more preferably, 5 to 50 wt %; still more preferably, 7.5 to 35 wt %, most preferably, 10 to 20 wt %), based on weight of the skin cleansing formulation, of a dermatologically acceptable personal care cleansing surfactant, wherein the dermatologically acceptable personal care cleansing surfactant is selected from the group consisting of alkyl polyglucosides (e.g., lauryl glucoside, coco-glucoside, decyl glucoside), glycinates (e.g., sodium cocoyl glycinate), betaines (e.g., alkyl betaines such as cetyl betaine and amido betaines such as cocamidopropyl betaine), taurates (e.g., sodium methyl cocoyl taurate), glutamates (e.g., sodium cocoyl glutamate), sarcosinates (e.g., sodium lauroyl sarcosinate), isethionates (e.g., sodium cocoyl isethionate, sodium lauroyl methyl isethionate), sulfoacetates (e.g., sodium lauryl sulfoacetate), alaninates (e.g., sodium cocoyl alaninate), amphoacetates (e.g., sodium cocoamphoacetate), sulfates (e.g., sodium laureth sulfate), sulfonates (e.g., sodium $C_{14-16}$ olefin sulfonate), succinates (e.g., disodium lauryl sulfosuccinate) and mixtures thereof. Yet more preferably, the skin cleansing formulation of the present invention is a body wash formulation, comprising 25 to 99 wt % (preferably, 30 to 90 wt %; more preferably, 60 to 85 wt %; most preferably, 75 to 80 wt %), based on weight of the skin cleansing formulation, of a dermatologically acceptable vehicle (preferably, water); 0.05 to 5 wt % (preferably, 0.1 to 2.5 wt %; more preferably, 0.2 to 1 wt %; most preferably, 0.35 to 0.75 wt %), based on weight of the skin cleansing formulation, of a deposition aid polymer, wherein the deposition aid polymer is a cationic dextran polymer, comprising a dextran functionalized with quaternary ammonium groups; 0.5 to 40 wt % (preferably, 1 to 15 wt %; more preferably, 2.5 to 7.5 wt %), based on weight of the skin cleansing formulation, of a dermatologically acceptable oil; wherein the dermatologically acceptable oil is selected from the group consisting of at least one of mineral oil, petroleum jelly, sunflower oil, soybean oil, coconut oil, silicone oil and fragrance oil; and 0.01 to 80 wt % (more preferably, 5 to 50 wt %; still more preferably, 7.5 to 35 wt %, most preferably, 10 to 20 wt %), based on weight of the skin cleansing formulation, of a dermatologically acceptable personal care cleansing surfactant; wherein the skin cleansing formulation is a body wash formulation and wherein the dermatologically acceptable personal care cleansing surfactant is selected from the group consisting of alkyl polyglucosides (e.g., lauryl glucoside, coco-glucoside, decyl glucoside), glycinates (e.g., sodium cocoyl glycinate), betaines (e.g., alkyl betaines such as cetyl betaine and amido betaines such as cocamidopropyl betaine), taurates (e.g., sodium methyl cocoyl taurate), glutamates (e.g., sodium cocoyl glutamate), sarcosinates (e.g., sodium lauroyl sarcosinate), isethionates (e.g., sodium cocoyl isethionate, sodium lauroyl methyl isethionate), sulfoacetates (e.g., sodium lauryl sulfoacetate), alaninates (e.g., sodium cocoyl alaninate), amphoacetates (e.g., sodium cocoamphoacetate), sulfates (e.g., sodium laureth sulfate), sulfonates (e.g., sodium $C_{14-16}$ olefin sulfonate), succinates (e.g., disodium lauryl sulfosuccinate) and mixtures thereof. Yet still more preferably, the skin cleansing formulation of the present invention is a body wash formulation, comprising 25 to 99 wt % (preferably, 30 to 90 wt %; more preferably, 60 to 85 wt %; most preferably, 75 to 80 wt %), based on weight of the skin cleansing formulation, of a dermatologically acceptable vehicle (preferably, water); 0.05 to 5 wt % (preferably, 0.1 to 2.5 wt %; more preferably, 0.2 to 1 wt %; most preferably, 0.35 to 0.75 wt %), based on weight of the skin cleansing formulation, of a deposition aid polymer, wherein the deposition aid polymer is a cationic dextran polymer, comprising a dextran functionalized with quaternary ammonium groups; 0.5 to 40 wt % (preferably, 1 to 15 wt %; more preferably, 2.5 to 7.5 wt %), based on weight of the personal care formulation, of a dermatologically acceptable oil; wherein the dermatologically acceptable oil includes mineral oil; and 0.01 to 80 wt % (more preferably, 5 to 50 wt %; still more preferably, 7.5 to 35 wt %, most preferably, 10 to 20 wt %), based on weight of the skin cleansing formulation, of a dermatologically acceptable personal care cleansing surfactant; wherein the skin cleansing formulation is a body wash formulation and wherein the dermatologically acceptable personal care cleansing surfactant comprises a mixture of sodium laureth sulfate (SLES) and cocamidopropyl betaine. Most preferably, the skin cleansing formulation of the present invention is a body wash formulation, comprising 25 to 99 wt % (preferably, 30 to 90 wt %; more preferably, 60 to 85 wt %; most preferably, 75 to 80 wt %), based on weight of the skin cleansing formulation, of a dermatologically acceptable vehicle (preferably, water); 0.05 to 5 wt % (preferably, 0.1 to 2.5 wt %; more preferably, 0.2 to 1 wt %; most preferably, 0.35 to 0.75 wt %), based on weight of the skin cleansing formulation, of a deposition aid polymer, wherein the deposition aid polymer is a cationic dextran polymer, comprising a dextran functionalized with quaternary ammonium groups; 0.5 to 40 wt % (preferably, 1 to 15 wt %; more preferably, 2.5 to 7.5 wt %), based on weight of the skin cleansing formulation, of a dermatologically acceptable oil; wherein the dermatologically acceptable oil is sunflower oil; and 0.01 to 80 wt % (more preferably, 5 to 50 wt %; still more preferably, 7.5 to 35 wt %, most preferably, 10 to 20 wt %), based on weight of the skin cleansing formulation, of a dermatologically acceptable personal care cleansing surfactant; wherein the skin cleansing formulation is a body wash formulation and wherein the dermatologically acceptable personal care cleansing surfactant comprises a mixture of sodium laureth sulfate (SLES) and cocamidopropyl betaine.

Preferably, the method of making a skin cleansing formulation of the present invention, comprises: (a) providing a dermatologically acceptable vehicle; (b) providing a dermatologically acceptable oil; (c) selecting a cationic dextran polymer as a deposition aid for enhancing deposition of the dermatologically acceptable oil onto mammalian skin; wherein the cationic dextran polymer comprises a dextran polymer functionalized with quaternary ammonium groups; (d) providing the selected cationic dextran polymer; and (d) combining the dermatologically acceptable vehicle, the dermatologically acceptable oil and the cationic dextran polymer to form a skin cleansing formulation. More preferably, the method of making a skin cleansing formulation of the present invention, comprises: (a) providing a dermatologically acceptable vehicle; (b) providing a dermatologically acceptable oil; (c) providing a dermatologically acceptable personal care cleansing surfactant; (d) selecting a cationic dextran polymer as a deposition aid for enhancing deposition of the dermatologically acceptable oil onto mammalian skin; wherein the cationic dextran polymer comprises a dextran polymer functionalized with quaternary ammonium groups; (e) providing the selected cationic dextran polymer; and (f) combining the dermatologically acceptable vehicle, the dermatologically acceptable oil, the dermatologically acceptable personal care cleansing surfactant and the cationic dextran polymer to form a skin cleansing formulation. Most preferably, the method of making a skin cleansing formulation of the present invention, comprises: (a) providing a dermatologically acceptable vehicle; (b) providing a dermatologically acceptable oil; (c) providing a dermatologically acceptable personal care cleansing surfactant; (d) providing at least one additional ingredient selected from the group consisting of an antimicrobial agent, a rheology modifier, a soap, a colorant, pH adjusting agent, an antioxidant, a humectant, a wax, a foaming agent, an emulsifying agent, a fragrance, a chelating agent, a preservative, a bleaching agent, a lubricating agent, a sensory modifier, a sunscreen additive, a vitamin, a protein/amino acid, a plant extract, a natural ingredient, a bioactive agent, an anti-aging agent, a penetrant, an anti-static agent, an absorbent, a hard particle, a soft particle, a slip agent, an opacifier, a pearlizing agent and a salt; (e) selecting a cationic dextran polymer as a deposition aid for enhancing deposition of the dermatologically acceptable oil onto mammalian skin; wherein the cationic dextran polymer comprises a dextran polymer functionalized with quaternary ammonium groups; (f) providing the selected cationic dextran polymer; and (g) combining the dermatologically acceptable vehicle, the dermatologically acceptable oil, the dermatologically acceptable personal care cleansing surfactant, the at least one additional ingredient and the cationic dextran polymer to form a skin cleansing formulation.

Preferably, the method of depositing a dermatologically acceptable oil onto mammalian skin of the present invention, comprises: providing a skin cleansing formulation of the present invention; and applying the skin cleansing formulation to the skin of a mammal. More preferably, the method of depositing a dermatologically acceptable oil onto mammalian skin of the present invention, further comprises: rinsing the skin cleansing formulation from the mammalian skin with a rinse water. Most preferably, the method of depositing a dermatologically acceptable oil onto mammalian skin of the present invention, comprises: selecting a skin cleansing formulation of the present invention; applying the skin cleansing formulation to mammalian skin; and rinsing the skin cleansing formulation from the mammalian skin; wherein the skin cleansing formulation is preferably a body wash (preferably, wherein the at least 10 wt % (more preferably, at least 12 wt %; most preferably, at least 15 wt %) of the dermatologically acceptable oil from the skin cleansing formulation is deposited on the mammalian skin).

Some embodiments of the present invention will now be described in detail in the following Examples.

Example S1: Synthesis of Cationic Dextran Polymer

A 500 mL, four necked, round bottom flask fitted with a rubber serum cap, a nitrogen inlet, a pressure equalizing addition funnel, a stirring paddle and motor, a subsurface thermocouple connected to a J-KEM controller and a Friedrich condenser connected to a mineral oil bubbler was charged with dextran (30.59 g; Sigma/Aldrich product D4876, molecular weight 130-170 kDa) and deionized water (140.75 g). The addition funnel was charged with a 70% aqueous solution of 2,3-epoxypropyltrimethylammonium chloride (27.14 g; QUAB® 151 available from SKW QUAB Chemicals). The flask contents were allowed to stir until the dextran dissolved in the deionized water. While the contents were stirring, the apparatus was purged with nitrogen to displace any oxygen entrained in the system. The nitrogen flow rate was about 1 bubble per second. The mixture was purged with nitrogen while stirring for one hour. Using a plastic syringe, a 25% aqueous sodium hydroxide solution (4.75 g) was added over a period of a few minutes to the flask contents with stirring under nitrogen. The flask contents were then allowed to stir under nitrogen for 30 minutes. The contents of the addition funnel were then charged to the flask contents dropwise over a few minutes under nitrogen with continued stirring. After the contents of the addition funnel were transferred to the flask contents, the mixture was allowed to stir for 5 minutes. Then heat was applied to the flask contents with a heating mantle controlled using the J-KEM controller set at 70° C. The flask contents were heated to and maintained at 70° C. for 90 minutes. The flask contents were then cooled to room temperature while maintaining a positive nitrogen pressure in the flask. When the flask contents reached room temperature, acetic acid (2.50 g) was added dropwise to the flask contents via a syringe and the mixture was stirred for 5 minutes. The polymer was recovered by non-solvent precipitation of this aqueous solution with an excess of methanol. The precipitated cationic dextran polymer was then recovered by filtration through a Buchner funnel and dried overnight in vacuo at 50° C. The product branched chain cationic dextran polymer was an off-white solid (29.8 g), with a volatiles content of 3.80%, an ash content of 0.03% (as sodium chloride). The volatiles and ash were measured as described in ASTM method D-2364. The Kjeldahl nitrogen content was measured using a Buchi KjelMaster K-375 automated analyzer, and was found to be 1.58% (corrected for volatiles and ash), which corresponds to a trimethylammonium degree of substitution of 0.22.

Example S2: Synthesis of Cationic Dextran Polymer

A 500 mL, four necked, round bottom flask fitted with a rubber serum cap, a nitrogen inlet, a pressure equalizing addition funnel, a stirring paddle and moter, a subsurface thermocouple connected to a J-KEM controller and a Freidrich condenser connected to a mineral oil bubbler was charged with dextran (30.5 g; Aldrich product #D4876) and deionized water (141 g). The addition funnel was charged with a 70% aqueous solution of 2,3-epoxypropyltrimethylammonium chloride (21.7 g; QUAB® 151 available from QUAB Chemicals). The flask contents were allowed to stir until the dextran dissolved in the deionized water. While the contents were stirring, the apparatus was purged with nitrogen to displace any oxygen entrained in the system. The nitrogen flow rate was about 1 bubble per second. The mixture was purged with nitrogen while stirring for one hour. Using a plastic syringe, a 25% aqueous sodium hydroxide solution (4.75 g) was added over a period of a few minutes to the flask contents with stirring under nitrogen. The flask contents were then allowed to stir under nitrogen for 30 minutes. The contents of the addition funnel were then charged to the flask contents dropwise over a few minutes under nitrogen with continued stirring. After the contents of the addition funnel were transferred to the flask contents, the mixture was allowed to stir for 5 minutes. Then heat was applied to the flask contents with a heating mantle controlled using the J-KEM controller set at 70° C. The flask contents were heated to and maintained at 70° C. for 90 minutes. The flask contents were then cooled to room temperature while maintaining a positive nitrogen pressure in the flask. When the flask contents reached room temperature, glacial acetic acid (2.5 g) was added dropwise to the flask contents via a syringe. The flask contents were then allowed to stir for 5 minutes. An excess of methanol was then added to the flask contents with vigorous stirring to precipitate cationic dextran polymer from solution. The precipitated cationic dextran polymer was then recovered by filtration through a Buchner funnel and dried overnight in vacuo at 50° C. The product cationic dextran polymer was an off-white solid (29.8 g), with a volatiles content of 3.80%, an ash content of 0.03% (as sodium chloride), and a Kjeldahl nitrogen content of 1.59%, which is equivalent to a degree of cationic substitution of 0.211.

Comparative Examples C1-C3 and Example 1: Body Wash Formulations

Body wash formulations were prepared in each of Comparative Examples C1-C3 and Example 1 by combining the components in the amounts listed in TABLE 1.

TABLE 1

| | Formulation (in wt %) | | | |
| --- | --- | --- | --- | --- |
| Component | C1 | C2 | C3 | 1 |
| Deionized water | q.s. 100 | q.s. 100 | q.s. 100 | q.s. 100 |
| Guar hydroxypropyltrimonium chloride[1] | — | 0.4 | — | — |
| Polyquaternium-10[2] | — | — | 0.4 | — |
| Product of Example S1 | — | — | — | 0.4 |
| Sodium laureth sulfate[3] | 48.0 | 48.0 | 48.0 | 48.0 |
| Cocamidopropyl betaine[4] | 8.5 | 8.5 | 8.5 | 8.5 |
| Sunflower Oil[5] | 5.0 | 5.0 | 5.0 | 5.0 |
| Acrylate copolymer[6] (28 wt % solids) | 11.4 | 7.14 | 8.44 | 4.44 |
| Propylene glycol (and) Dizzolidinyl Urea (and) Iodopropynyl Butylcarbamate[7] | 1.0 | 1.0 | 1.0 | 1.0 |
| 24 hr viscosity—spindle 5 @ 10 rpm (cps) | 9,200 | 8,080 | 8,000 | 10,000 |

[1]EcoSmooth ™ 100 guar hydroxypropy trimonium chloride available from The Dow Chemical Company
[2]UCARE ™ JR 30M available from The Dow Chemical Company
[3]Steol CS-130 sodium laureth sulfate (aq. 25 wt %) a vailable from Stepan Company
[4]Amphosol CA cocamidopropyl betaine (aq. 30 wt % ) available from Stepan Company
[5]from Spectrum
[6]Aculyn ™ 33 acrylates copolymer avaiable from The Dow Chemical Company
[7]Liquid Germall Plus available from Ashland Chemical

Performance Testing

The body wash formulations from each of Comparative Examples C1-C3 and Example 1 were titrated to a pH of 6.5 with citric acid (25% in water). The final compositions were then applied to a Vitro-Skin® advanced testing substrate (available from IMS Inc.) using a cot covered finger. The treated substrates were then rinsed with deionized water and evaluated for deposition of oil onto the substrate. Eight replicate Vitro-Skin® advanced testing substrate samples were prepared for each of the skin cleansing formulations. The following procedure was used: (a) Vitro-Skin® advanced testing substrate was cut into 4 cm×4 cm pieces; (b) Each test substrate was weighted; (c) Using a 1 mL HSW syringe (Henke Saas Wolf GmbH), a 0.2 mL sample of the skin cleansing formulation was deposited onto the rough side of the test substrate; (d) Using a cot covered finger, the deposited skin cleansing formulation was then gently rubbed on the substrate for about 15 seconds; (e) Each test substrate was weighted again following treatment with the skin cleansing formulation; (f) Each treated substrate was set aside for 20 seconds before rinsing with water; (g) Each treated substrate was then rinsed with water at a flow rate of 1 L/min with a water temperature of 32 to 38° C. The rough surface (surface on which the skin cleansing formulation was applied) faced the flow of rinse water at a 45° angle, 5 to 10 cm from the faucet outlet for 15 seconds; (h) Each rinsed substrate was then placed in a clean tray with the treated surface facing up and left to dry for an hour before proceeding with a sunflower oil deposition analysis.

Sunflower Oil Deposition Analysis

The sunflower oil deposition on Vitro-Skin® advanced testing substrate was quantified by two dimensional gas chromatography mass spectrometry (2D-GC/MS) analysis.

Sample preparation: Each rinsed skin deposition sample (one piece of 4 cm×4 cm) was then placed in a 1 oz vial filled with 20 mL of hexane. Samples were then shaken for 1.5 hours on a shaker. A portion of the liquid in each vial (5 mL) was then transferred to a separate 10 mL vial. To each 10 mL vial was then added 5 mL of a 1M KOH/MeOH solution. The 10 mL vials were then placed on the shaker for an hour followed by 30 minutes resting for settlement. The hexane layer was then filtered from each 10 mL vial into an autosampler vial using 0.2 µm PTFE filter and analyzed by GC/MS.

2D-GC/MS condition: An Agilent 7890B GC equipped with a flame ionization detector (FID) and a 5977A mass selective detector (MSD) was used for the analysis of sunflower oil. The GC conditions are listed below in TABLE 2.

TABLE 2

| Instrument | Agilent 7890B GC with 5977A MSD with Extractor EI source |
|---|---|
| Column: | DB-WaxUI, 30 m × 0.25 mm × 0.25 µm film |
| GC Oven: | Initial 150° C. (hold 1 minute) to 250° C. at 10° C./minute (hold 1 minute); Total run time: 12 minutes |
| Injection volume: | 1 µL |
| Inlet | Temperature: 250° C. Split ratio: 10:1 Carrier gas: Helium |
| MSD Parameters: | Transfer line temperature: 250° C. EI source temperature: 230° C. Quad temperature: 150° C. EM voltage: 2135 V Energy: 70 eV Emission: 35 µA SIM ion: m/z 264.3 |

The external calibration was applied for obtaining the response factor of sunflower oil. A 1,000 mg/L stock solution was prepared by weighing 10 mg of sunflower oil into a 20 mL vial and adding 10 mL of hexane to the vial to make exact concentration of 1,000 mg/L. Calibration standard solutions with concentration levels of 1, 2, 5, 10, 20, 50, 100, 200 and 500 mg/L were prepared from serial dilution from the stock solution using hexane as the diluent. 2 mL of each standard solution and 200 µL of 1 M KOH/MeOH solution were combined into a 5 mL vial. Each solution was shaken for one hour and then settled for 30 minutes in a lab hood until clear phase separation was obtained. Approximately 350 µL of the top hexane layer was then transferred to a low-volume autosampler vial (with insert) for GC analysis.

The percent deposition of sunflower oil was calculated using the equation below:

$$\text{Deposition \%} = (((W \times \text{sunflower oil wt \%})/v)/C)$$

wherein Deposition % is the wt % of sunflower oil from the applied formulation remaining on the Vitro-Skin® advanced testing substrate; wherein C is the concentration of sunflower oil in the extraction solvent measured by 2D-GC/MS in mg/mL; wherein W is the weight of formulation applied onto the Vitro-Skin® advanced testing substrate in mg; wherein sunflower oil wt % is the concentration of sunflower oil in the formulation applied in wt %; and wherein v is the volume of hexane added into the formulation applied in mL. The results are provided in TABLE 3.

TABLE 4

| Body wash formulation | Sunflower oil wt % deposition |
|---|---|
| Comparative Example C1 | 10.65 |
| Comparative Example C2 | 27.54 |
| Comparative Example C3 | 19.34 |
| Example 1 | 15.67 |

We claim:
1. A skin cleansing formulation, comprising:
 a dermatologically acceptable personal care cleaning surfactant;
 40 to 90 wt %, based on weight of the skin cleansing formulation, of a dermatologically acceptable vehicle;
 2.5 to 15 wt %, based on weight of the skin cleansing formulation, of a dermatologically acceptable oil, wherein the dermatologically acceptable oil is selected from the group consisting of hydrocarbon oils, natural oils, fragrance oils and mixtures thereof; and
 0.2 to 1 wt %, based on weight of the skin cleansing formulation, of a deposition aid polymer, wherein the deposition aid polymer is a cationic dextran polymer, comprising a dextran polymer functionalized with quaternary ammonium groups, wherein the dextran polymer is a branched chain dextran polymer;
 wherein the skin cleansing formulation comprises less than 0.0001 wt %, based on weight of the skin cleansing formulation, of silicone;
 wherein the deposition aid polymer enhances the deposition of the dermatologically acceptable oil from the skin cleansing formulation onto mammalian skin.

2. The skin cleansing formulation of claim 1, wherein the cationic dextran polymer has a Kjeldahl nitrogen content corrected for ash and volatiles, TKN, of 1.0 to 4.0 wt %.

3. The skin cleansing formulation of claim 2, wherein the quaternary ammonium groups are selected from the group consisting of trialkyl ammonium moieties of formula (B) bound to the dextran polymer

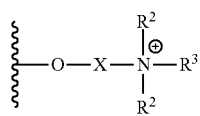

(B)

wherein

is the dextran polymer with a pendant oxygen; wherein X is a divalent linking group bonding the trialkyl ammonium moieties to pendent oxygen on the dextran polymer;

wherein each $R^2$ is independently selected from the group consisting of a $C_{1-7}$ alkyl group; and wherein $R^3$ is selected from the group consisting of a $C_{1-22}$ alkyl group.

4. The skin cleansing formulation of claim 3, wherein X is a —$CH_2CH(OR^4)CH_2$— group; wherein $R^4$ is selected from the group consisting of a hydrogen and a $C_{1-4}$ alkyl group.

5. The skin cleansing formulation of claim 4, wherein each $R^5$ is a methyl group.

6. The skin cleansing formulation of claim 5, wherein the dermatologically acceptable personal care cleaning surfactant comprises a mixture of sodium laureth sulfate (SLES) and cocamidopropyl betaine; and wherein the dermatologically acceptable oil is a natural oil selected from the group consisting of caprylic and capric triglyceride, sunflower oil, soybean oil and coconut oil.

7. A method of making a skin cleansing formulation, comprising:
  (a) providing a dermatologically acceptable vehicle;
  (b) providing a dermatologically acceptable oil, wherein the dermatologically acceptable oil is selected from the group consisting of hydrocarbon oils, natural oils, fragrance oils and mixtures thereof;
  (c) selecting a cationic dextran polymer to be a deposition aid for enhancing deposition of the dermatologically acceptable oil onto mammalian skin; wherein the cationic dextran polymer comprises a dextran polymer functionalized with quaternary ammonium groups; wherein the dextran polymer is a branched chain dextran polymer; and
  (d) combining the dermatologically acceptable vehicle, the dermatologically acceptable oil and the cationic dextran polymer to form a skin cleansing formulation; wherein the skin cleansing formulation comprises less than 0.0001 wt %, based on weight of the skin cleansing formulation, of silicone.

8. A method of depositing a dermatologically acceptable oil onto mammalian skin, comprising:
  providing a skin cleansing formulation according to claim 1; and
  applying the skin cleansing formulation to the skin of a mammal.

9. The skin cleansing formulation of claim 1, wherein the silicone is selected from the group consisting of dimethylpolysiloxane, methylphenyl polysiloxane, polyether denaturation silicone oil and polyamino modifying silicone oil.

10. The skin cleansing formulation of claim 6, wherein the natural oil is sunflower oil.

11. The skin cleaning formulation of claim 10, wherein the silicone is selected from the group consisting of dimethylpolysiloxane, methylphenyl polysiloxane, polyether denaturation silicone oil and polyamino modifying silicone oil.

12. The method of claim 7, wherein the silicone is selected from the group consisting of dimethylpolysiloxane, methylphenyl polysiloxane, polyether denaturation silicone oil and polyamino modifying silicone oil.

13. The method of claim 8, wherein the silicone is selected from the group consisting of dimethylpolysiloxane, methylphenyl polysiloxane, polyether denaturation silicone oil and polyamino modifying silicone oil.

* * * * *